US006689568B2

(12) United States Patent
Myerson

(10) Patent No.: US 6,689,568 B2
(45) Date of Patent: Feb. 10, 2004

(54) CAPTURE ARRAYS USING POLYPEPTIDE CAPTURE AGENTS

(75) Inventor: Joel Myerson, Berkeley, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 0 days.

(21) Appl. No.: 09/773,886

(22) Filed: Feb. 1, 2001

(65) Prior Publication Data

US 2002/0102605 A1 Aug. 1, 2002

(51) Int. Cl.[7] ................................................ G01N 33/53
(52) U.S. Cl. ............................ 435/7.1; 435/6; 436/501; 436/504; 436/544; 436/545; 436/546
(58) Field of Search ............................ 435/6, DIG. 15, 435/DIG. 41, 7.1; 436/501, 86, 546, 544, 545

(56) References Cited

U.S. PATENT DOCUMENTS 5,367,058 A * 11/1994 Pitner et al. ............. 530/391.9
5,869,644 A   2/1999 Shortle et al.

FOREIGN PATENT DOCUMENTS

| WO | WO 00/00632 | 1/2000 |
| WO | WO 00/04775 | 2/2000 |
| WO | WO 00/18778 | 4/2000 |
| WO | WO 00/32823 | 6/2000 |
| WO | WO 00/72869 | 12/2000 |

OTHER PUBLICATIONS

Janeway, C. A.; Travers, P.; Immunobiology. Garland Publishing Inc, New York, 1997.*
Kalluri R.; Gunwar, S.; Reeders, S. T.; Morrison, K. C.; Mariyama, M.; Ebner, K.E.; Noelken, M. E.; Hudson, B. G. J. Biol. Chem. 1991, 266(35), 24018–24024.*
Richard Roberts and Jack Szostack "RNA–peptide fusions for the in–vitro selection of peptides and proteins" Proc. Natl. Acad. Sci. USA, vol. 94, pp. 12297–12302, Nov. 1997.
Wilson and Szostak "In Vitro Selection of Functional Nucleic Acids" Annu. Rev. Biochem, 1999, 68:611–647.
Josef Brunner " Biosynthetic Incorporation of Non–naturenal Amino Acids Into Proteins" Chemical Society Reviews 1993, 183–189.
Gilmore et al. "Incorporation of non–coded amino acids by in vitro protein biosythesis" Top. Curr. Chem 202: 77–99 (1999).

* cited by examiner

Primary Examiner—Bennett Celsa
Assistant Examiner—Jon D. Epperson
(74) Attorney, Agent, or Firm—Timothy H. Joyce

(57) ABSTRACT

A method of evaluating for the presence of a polypeptide in an analyte, using an addressable array of capture agents linked to a substrate. The analyte is exposed to the array and a set of fixed capture agents, such that the target molecules will bind to the array by means of the capture agents. After the target molecule has bound to the capture agents, it is modified using a label. The label does not interact or mark the capture agent. Kits using such arrays are further provided.

29 Claims, 5 Drawing Sheets

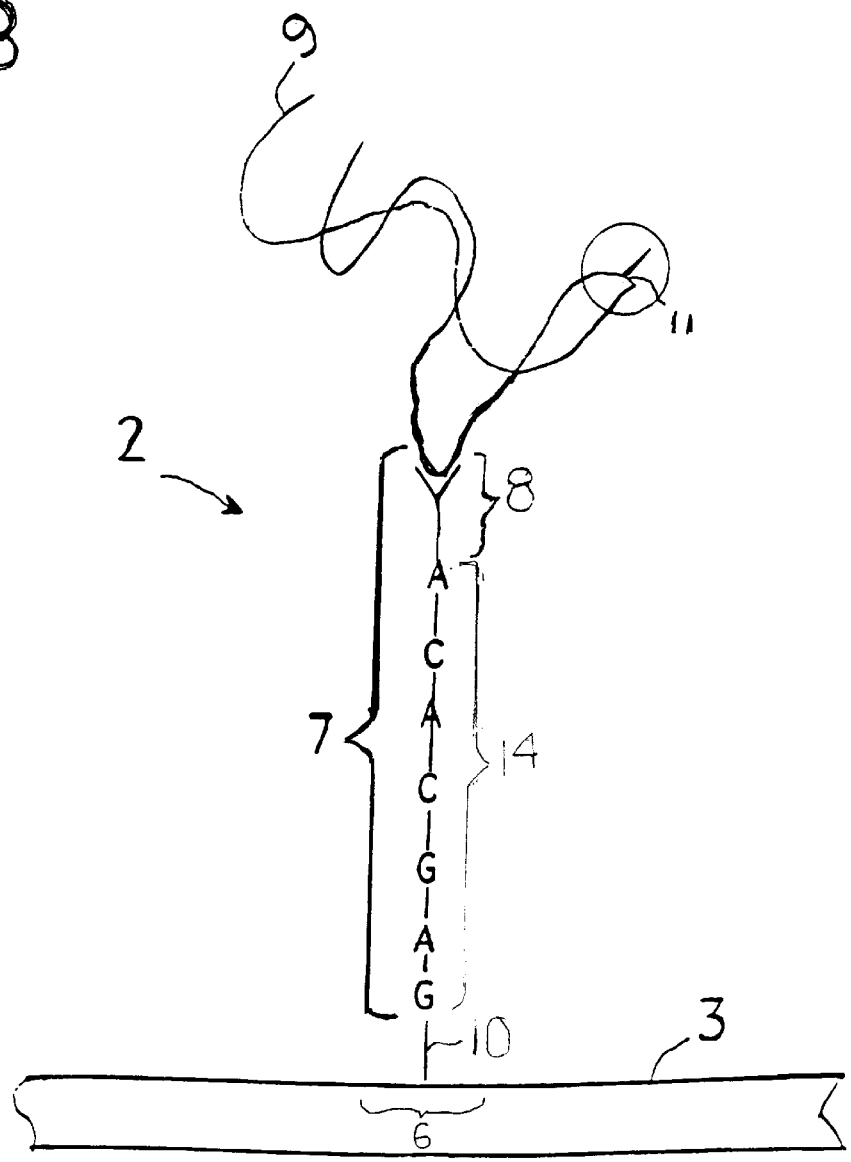

CAPTURE ARRAYS USING POLYPEPTIDE CAPTURE AGENTS

FIELD OF THE INVENTION

This invention relates to arrays, and more particularly to capture arrays using polypeptide, peptide and protein fragments for the detection of other proteins or amino acid oligomers.

BACKGROUND OF THE INVENTION

Various arrays have been designed for use in genetic testing, screening and diagnostics. Most of the arrays that have been developed include the use of defined regions having biopolymers or nucleotides arranged in a predetermined configuration on a defined substrate. Most importantly, these arrays when exposed to a particular analyte will exhibit a pattern indicative of the presence and concentration of a particular component, peptide or oligonucleotide. Array binding patterns using polynucleotides and/or peptides can be detected by using a variety of suitable fluorescent target labels. Once bound to the array, the overall fluorescence pattern on the array is determined and the target labels can then be quantified and observed.

Arrays using proteins, peptides and protein fragments have been gaining much attention. Using these types of arrays, various techniques can be used to identify and capture various proteins of interest. Construction of this type of array can be used to effectively capture proteins of interest. Arrays for capturing proteins can be made using polypeptide capture agents such as antibodies, antibody fragments, or polypeptides selected from randomized or combinatorial libraries by means of phage display, ribosome display, or mRNA-protein fusion. However, there is a particular difficulty and disadvantage in using an array of amino acid oligomers to detect other proteins. In the first instance, there is the possibility of cross reactivity between the capture probe and the wrong protein. However, more importantly, the array needs to distinguish the protein-capture agent complex from the capture agents themselves.

A number of techniques have been developed for actually distinguishing the capture agents from the target agents or proteins, or from the capture agent/target complex. For instance, measurements can be done by using techniques such as ellipsometry, surface plasmon resonance, or microbalances based on surface acoustic waves. Other approaches require tagging or labeling the target agent or protein with a reagent that can be detected. For instance, detection of tags or labels can be done using optical or electrochemical technology. These latter tagging methods, which include direct optical techniques such as fluorescence, as well as indirect visualization by means of a biotin tag and subsequent avidin complexation, require that the target proteins be labeled with a tag before the assay is performed. Labeling the bound protein after the assay is performed is not feasible because the capture agents, that are amino acid oligomers, (e.g. antibodies) will also be labeled. Thus, the array feature with or without a bound target present will most likely then give a false positive response or reading.

A number of solutions have been proposed to the labeling problems discussed above. For instance, labeling the target molecules before the assay is performed gets around the problem of false positive responses that is due to the undesired reaction of the tag with the capture agent. However, this has many disadvantages. For example the unreacted tag can interfere with the binding assay, extra purification may need to be performed, or the modification of the protein with a tag may seriously affect the binding behavior of the protein (i.e. the $K_d$ or selectivity may be altered or affected). It would be desirable therefore, to provide a means for detecting a target or target protein using polypeptide probes, particularly in the form of an addressable array, which can provide good binding affinity and specificity for a target protein or polypeptide. It would also be desirable to combine the strengths of the above technology to construct an array based system or methodology for protein analysis that is rapid, efficient and that is amenable to protein monitoring applications. In addition, it would be desirable to develop capture agents for use in an array that can detect amino acids, peptides or proteins (i.e. oligomer targets) without the need for pre-derivatization of the target. It would also be preferable to have a binding assay that can be done using unmodified targets, where detection is done after the targets have bound and after unbound targets have been washed away. Lastly, it would be desirable to have a system where specific tags can be used to react with the side chains on the target proteins, while the features of the array, consisting of amino acid oligomers, remain unchanged.

The references cited in this application, are incorporated in this application by reference. However, cited references are not admitted to be prior art to this application.

SUMMARY OF THE INVENTION

The invention is a method for detecting the presence of a target protein molecule using a polypeptide target probe. The target protein is not derivatized or pre-modified. Binding takes place between the target protein and the capture agent. The target protein is then modified for detection, while the capture agent remains unmodified for detection. The apparatus of the present invention includes an addressable array comprising a number of polypeptide capture agents designed to bind a particular target. The capture agents do not contain one or more defined amino acids with a modifiable side chain that may be used for detection. The target protein contains one or more of these same amino acids with modifiable side chains used in detection.

BRIEF DESCRIPTION OF THE DRAWINGS

Embodiments of the invention will now be described with reference to the drawings in which:

FIG. 3B shows a second schematic view of the present invention.

To facilitate understanding, identical reference numerals have been used, where practical, to designate similar elements that are common to the figures.

DETAILED DESCRIPTION OF THE INVENTION

Figure 1:
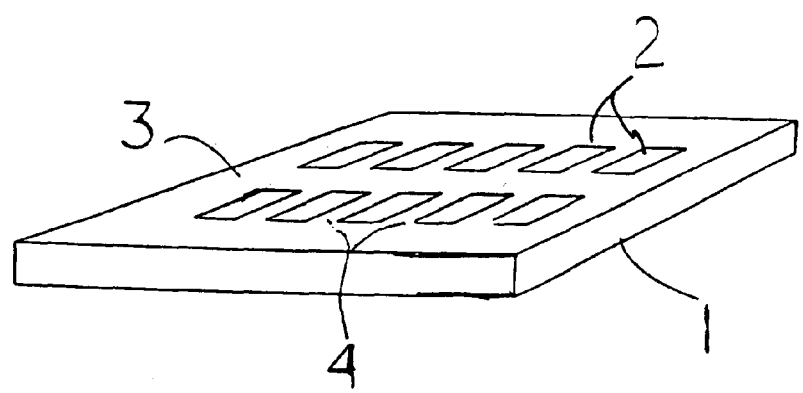
FIG. 1 illustrates a chip carrying polypeptide arrays, at least one of which is of the present invention, wherein the capture agents are directly linked to a substrate.

Before describing the present invention in detail, it is to be understood that this invention is not limited to specific compositions, process steps, or equipment, as such may vary. It is also to be understood that the terminology used herein is for the purpose of describing particular embodiments only, and is not intended to be limiting.

It must be noted that, as used in this specification and the appended claims, the singular forms "a", "an" and "the" include plural referents unless the context clearly dictates otherwise. Thus, for example, reference to "an array" includes more than one array, reference to "a polypeptide" includes a plurality of polypeptides and the like.

In describing and claiming the present invention, the following terminology will be used in accordance with the definitions set out below.

A "biopolymer" is a polymer of one or more types of repeating units. Biopolymers are found in biological systems and particularly include peptides and polypeptides, as well as such compounds composed of or containing amino acids or their analogs or non-peptide groups. This includes polypeptides in which the conventional backbone has been replaced with non-naturally occurring or synthetic backbones, and peptides in which one or more of the conventional amino acids have been replaced with a non-naturally occurring or synthetic amino acid capable of participating in peptide bonding interactions. Polypeptides include single or multiple stranded configurations, where one or more of the strands may or may not be completely aligned with another on the array surface. Specifically, a "biopolymer" includes amino acids and polypeptides, regardless of the source.

A "peptide" refers to a sub-unit of a polypeptide and has a carboxyl group and an amino group, as well as analogs of such sub-units.

A "polypeptide" refers to a multimer of about 10 to 100 amino acids in length, and includes a multimer having any number of amino acids.

A "biomonomer" refers to a single unit, which can be linked with the same or other biomonomers to form a biopolymer. A biomonomer fluid or biopolymer fluid reference a liquid containing either a biomonomer or biopolymer, respectively (typically in solution).

An "array", unless a contrary intention appears, includes any one, two or three dimensional arrangement(s) of addressable regions bearing particular biopolymer moieties (for example different polypeptide sequences) associated with that region. An array is "addressable" in that it has multiple regions of different moieties (for example, different sequences) such that a region at a predetermined location (an "address") on the array (a "feature" of the array) will detect a particular target or class of targets (although a feature may incidentally detect non-targets of the feature). In the present case, the polypeptide (or other) target will be in a mobile phase (typically fluid), while agents ("capture agents") may or may not be mobile. "Hybridizing" and "binding", with respect to polypeptides, are used interchangeably. "Binding efficiency" refers to the productivity of a binding reaction, measured as either the absolute or relative yield of binding product formed under a given set of conditions in a given amount of time. It will also be appreciated that throughout the present application, that words such as "upper", "lower" are used in a relative sense only. A "set" may have one type of member or multiple different types. "Fluid" refers to a liquid.

The term "capture agent/target complex" refers to any agent, complex, peptide, or polypeptide that is attached to an array surface and bound to other molecules or targets.

The term "fusion protein" refers to a polypeptide associated with its nucleic acid containing counterpart selected from a randomized or combinatorial library by means of phage display, ribosome display, mRNA or DNA-peptide fusions, or the like.

The term "variable region" and "non-variable region" refers to particular portions of an antibody or antibody fragment that are clearly defined and well known in the immunology art, as well as to capture agents prepared from a library of mRNA that contains randomized as well as constant regions.

The term "target" refers to any molecule, peptide or polypeptide that may be of known or unknown sequence that binds to the capture agent.

Figure 2:
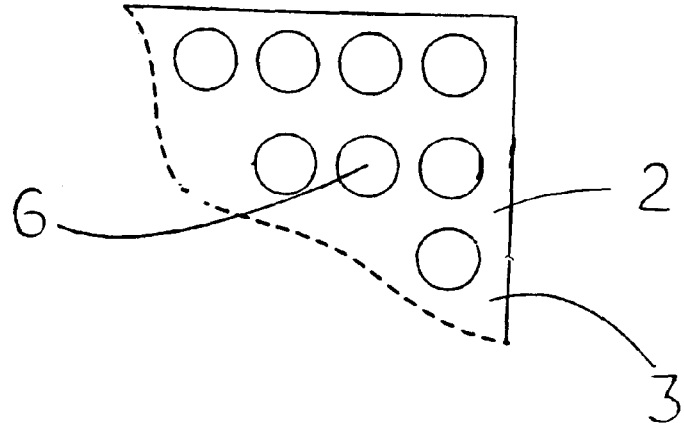
FIG. 2 is an enlarged view of a portion of FIG. 1 showing multiple spots or regions of the array that would contain the capture agents.
Figure 3A:
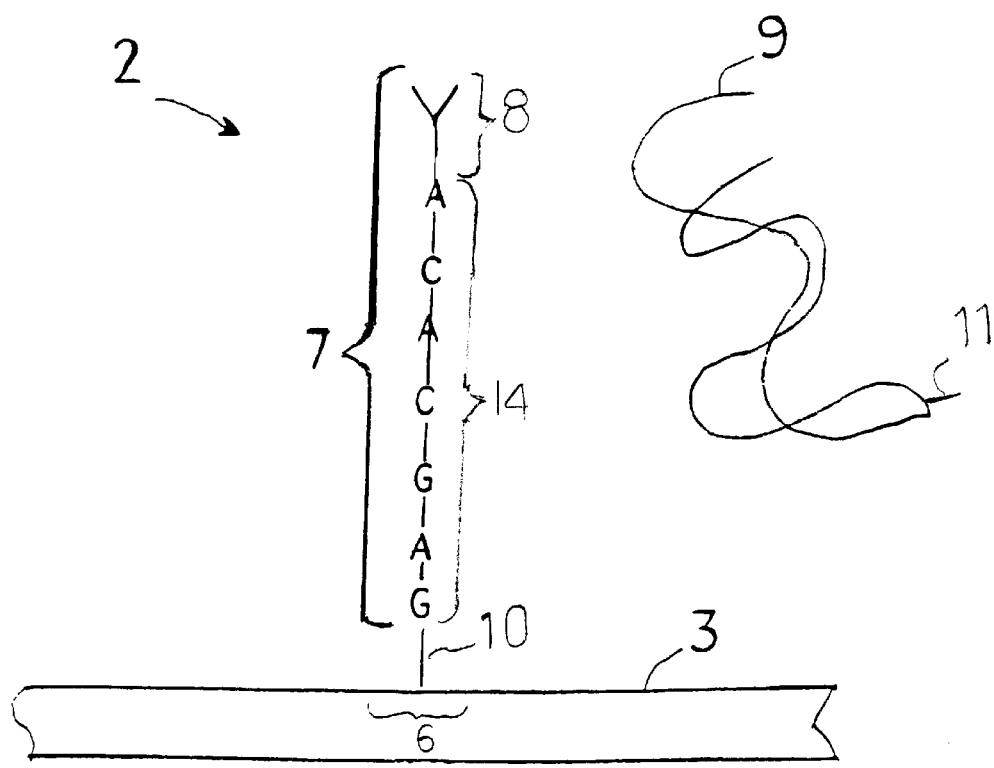
FIG. 3A shows a schematic view of the present invention.

Referring first to FIGS. 1–3, typical kits and methods of the present invention use a contiguous substrate 1 carrying arrays 2 disposed across an array surface 3 of substrate 1 and separated by areas 4. The arrays on substrate 1 can be designed for detecting an analyte or for evaluating capture agents on their ability to bind target molecules. While a number of arrays 2 are displayed and shown in FIG. 1, the different embodiments described below may use substrates with particular numbers of arrays, it will be understood that substrate 1 and the embodiments to be used with it may use any number of desired arrays 2. Similarly, substrate 1 may be of any shape, and any apparatus used with it adapted accordingly. Depending upon intended use, any or all of arrays 2 may be the same or different from one another and each will contain multiple spots or features 6 of biopolymers in the form of polypeptides. A typical array may contain from 10 to 100,000 regions. All of the features 6 may be different, or some or all could be the same. Each feature carries a predetermined polypeptide having a particular sequence, or a predetermined mixture of polypeptides. It will be appreciated though, that there need not be any space separating arrays 2 from one another, no features 6 within an array from one another. The apparatus and kits of the present invention are illustrated in FIG. 4. The kit 15 includes the capture agents 7 fixed to the array 2 and label 13. The kit 15 may also include an optional target 9. A brief description of the parts of the invention follows below. The capture agent 7 may comprise both an amino acid chain 14 and a binding domain 8. In certain instances it may also include the use of a linker or attachment point 10 connecting the amino acid chain 14, domain 8 or combination to array surface 3 (See FIG. 3A). The capture agent 7 may not include any amino acids that contain modifiable side chains used for detection. The diagram has been labeled using, "A", "C", and "G". The symbols stand for alanine, cysteine, and glycine respectively. The drawing is not intended to be to scale and the amino acids and sequences are for illustrative purposes only and should not be interpreted in any way to limit the broad scope of the invention. In addition, the amino acid chain 14 may comprise any number of amino acids. An important component of the invention is that the amino acid chain 14 and the binding domain 8 do not contain a defined amino acid that the target 9 has in its primary sequence. It should be noted that in certain instances the capture agent 7 and the target 9 may contain the same or similar amino acids with modifiable side chains, in which case, the side chains of the amino acids of the capture agent 7 have been rendered inactive or blocked e.g. by acetylation, other blocking agents known in the art, or is just not derivitizable because of e.g. steric effects. Creighton, T. E., Proteins, Structure and Molecular Properties, Second Edition, W. H. Freeman & Company, New York, 1993; pp. 86–104; Creighton, T. E., Protein Function, A Practical Approach, Oxford University Press, New York, 1990; pp. 101–132; 225–274.

Capture agent 7 is designed for binding a protein, peptide, polypeptide, or other molecule of a predetermined type.

Capture agent 7 generally comprises a linker or attachment point 10 for attaching the molecule to substrate surface 3, an amino acid chain 14, as described above, and a binding domain 8 for binding to target 9. Binding domain 8 can consist of a single domain or multiple domains, and need not be situated at the end of amino acid chain 14, but can be situated anywhere in or on capture agent 7. For clarity in the diagrams attachment point 10 is shown at the end of the molecule. However, the attachment point 10 may be in the middle of the molecule or any other convenient point. In addition, the invention should not be limited to just polypeptides that contain a standard amino and carboxyl terminus. For example, the invention also includes the circumstance where a single lysine is involved in attachment 10, and the polypeptide has a blocked N-terminus. Binding domain 8 is capable of binding a target molecule 9 under a variety of solutions and pH conditions. Attachment end 10 may be attached to substrate surface 3 using a variety of chemical reactions including condensation reactions, nucleophilic and electrophilic substitutions. Peptide bonds as well as reactions using the amino terminal and/or carboxyl end of amino acid chain 14 may be used to attach the capture agent 7. This may or may not include the use of side chain attachment. Other well-known chemistries in the art including disulfide bonds and the like may be used. Creighton, T. E., Proteins, Structure and Molecular Properties, Second Edition, W. H. Freeman & Company, New York, 1993; pp. 86–104; Creighton, T. E., Protein Function, A Practical Approach, Oxford University Press, New York, 1990; pp. 101–132; 225–274.

Capture agent 7 may also comprise a binding domain 8. Binding domain 8 may be defined by a number of specific and non-specific molecules capable of binding other molecules. For instance, binding domain 8 may be a complete antibody with variable and non-variable regions, an Fv, Fab or (Fab)₂ type fragment(s). Other molecules could include fibronectin or other similar molecules that are well known in the art. Binding domain 8 may also include combinations and parts of the above molecules. Janeway, C. A., Travers, P., Walport, M. & Capra, J. D., ImmunoBiology, The Immune System in Health and Disease, Fourth Edition, Elsevier Science Ltd., Garland Publishing, New York; 1999; pp.101–132; 225–274.

Target 9 may include a variety of peptide, protein, polypeptide, glycoprotein, amino acid or similar type molecules. The important point to the invention is target 9 contains a particular amino acid 11 that has a side-chain that is capable of being modified with a label 13 (e.g. arginine, lysine, cysteine, histidine, aspartic acid and glutamic acid) (See FIG. 3C). The capture agents 7 are designed so that they do not contain the same or similarly reactive amino acid 11, or if they do the side chain is non-reactive to modification with label 13 under conditions that the target amino acid 11 is reactive. This non-reactivity can be due to prior reaction of the side chain with a blocking agent, or steric and/or electronic effects that preclude modification with label 13. The label 13 used in the present invention is discussed in more detail below.

The label 13 is designed to modify amino acids 11 in the target 9. No modification of the capture agent 7 takes place. This allows for quantification of the target 9 as well as ease in discriminating the capture agent 7 from the target 9. Label 13 may comprise a variety of organic, inorganic or radioactive molecules for identifying the amount of target 9 present in an analyte. Typical labels are well known in the art and include fluorophores, ligands, radioisotopes, chemiluminescent molecules and bioluminescent molecules, as well as affinity reagents such as biotin, for subsequent labeling with molecules such as avidin. The important component of the chemistry is that the labeling agent must be capable of reacting with target molecule 9 while it is bound to binding domain 8, while not reacting with capture agent 7. Other well known labeling agents that are known in the art may also be used. For instance, the Molecular Probe catalog (Molecular Probes, Inc, 4849 Pitchford Av, Eugene, Oreg.) contains a number of various labeling agents and common chemistries that are well known in the art. This application does hereby incorporate these labels and chemistries by reference.

For instance, capture agents 7 are prepared that will not react with standard amino reactive tags. Targets 9 that are bound to capture agent 7 can be treated after the binding event has occurred, negating the need for a target pre-derivatization step. This is done by creating a capture agent 7 that does not include any amino acids with modifiable amino containing side chains, or by creating a capture agent 7 that has only one primary amine functionality, used for surface attachment. Ordinary methods for preparation of amino acid oligomer capture agents 7, such as antibody formation, are not suitable ways to prepare such molecules. A number of examples are presented below for preparing polypeptides that maintain strong binding affinity, yet do not contain a particular amino acid, for example, lysine in the capture agents 7.

Figure 3C:
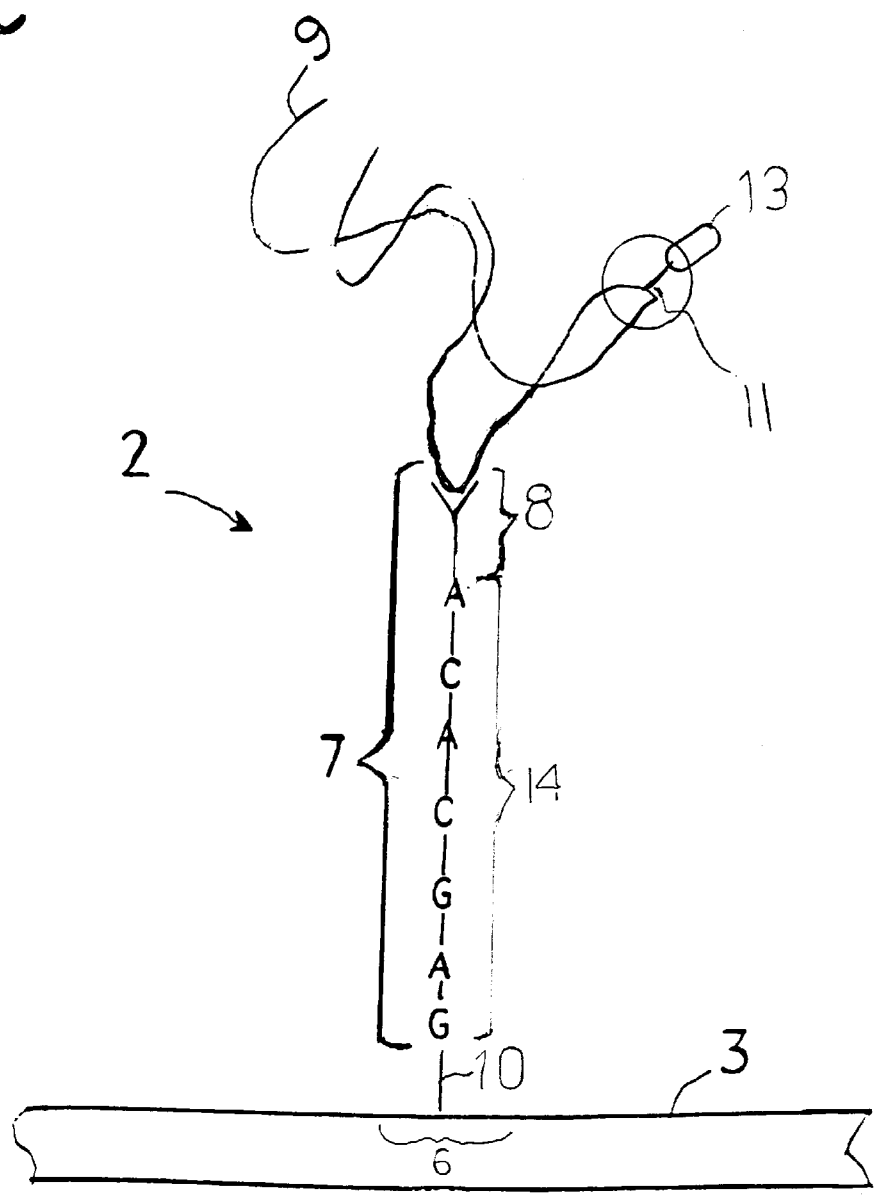
FIG. 3C shows a third schematic view of the present invention.
Figure 4:
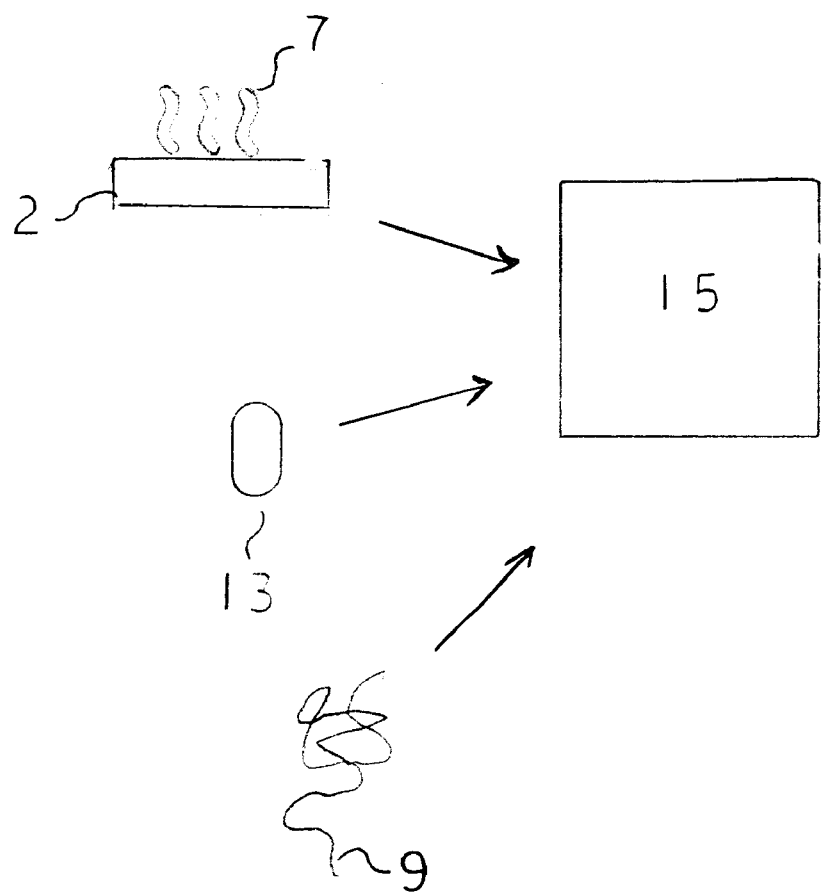
FIG. 4 illustrates a kit of the present invention.

FIGS. 3A–3C illustrates the steps and method of the present invention. The invention first step includes constructing an array with a capture agent 7 that does not contain an amino acid 11. The modifiable side chain of the amino acid 11 has been circled for clarification of its position in FIGS. 3B–C. The second step is binding a target molecule 9 to the capture agent 7 by means of the binding domain 8 (See FIG.3B). The final step is modifying a particular amino acid 11 or series of amino acids with a label 13 (See FIG. 3C). The label 13 does not modify any of the amino acids of the capture agent 7. The capture agent 7 and the target molecule 9 can, therefore, be easily distinguished. A variety of detection schemes can be used at this point including scanning devices and calibrating machines to determine the quantity and/or existence of the labels. These detection schemes and instruments are well known in the art.

A number of methods exist for construction of the arrays and capture agents described in this application. A few methods are described below. The nature and scope of the invention and how the capture agents are designed and produced, however, should not be interpreted to be limited to only those methods and procedures described below. In addition, the examples are provided for illustration purposes only and should not be construed to narrow the broad scope of the invention.

EXAMPLE 1

Modifications of an in vitro selection approach have been used for generation of the capture agents (e.g. Roberts, R. W.; Szostak, J. W., "RNA-peptide fusions for the in vitro selection of peptides and proteins", P. Natl Acad. Sci. USA 94: 12297–12302 (1997), Wilson, D. S. Szostak, J. W. "In vitro selection of functional nucleic acids", Annu Rev. Biochem. 68: 611–647 (1999). WO 9831700, WO 004775, WO 0032823). For instance, covalent fusions between an mRNA and the peptide or protein that it encodes can be generated in vitro by translation of synthetic mRNAs that carry puromycin. Puromycin is a peptidyl acceptor antibiotic that operates at the 3' end of the mRNA. The molecule helps form stable linkages or bonds between the information nucleic acid (i.e. template mRNA) and the functional peptide or expression product. This technique allows for the quick and efficient means to select a particular mRNA and its encoded product from a complex mixture of mRNAs that do not code for the peptide or protein of interest.

Standard molecular biology techniques, therefore, can be used to amplify the signals of the desired mRNA, so that ultimately a small number of associated proteins are selected for that have the desired capture agent properties. Used in the "standard" fashion, such a process will not result in a capture agent that is free of lysine or a particular amino acid that one desires to omit in a polypeptide sequence. This is an important aspect of the present invention. In order to obtain the desired product of the present invention, a number of additional and important steps must be taken. These methods or steps are discussed and described in more detail below.

EXAMPLE 2

First, the non-variable regions of the capture agents must be engineered so that no lysines or defined amino acids are present in the polypeptide or peptide. This is easily accomplished, because the nature of the selection process does not require any particular sequence, only that the end result has the desired properties. Omitting the lysines or replacing the lysines with a non-modifiable amino acid such as arginine is one possibility. Alternatively, in the absence of lysine, more extensive modifications may need to be performed in order to maintain the desired properties of the non-variable scaffold region.

Second, the lysines must be removed from the variable regions of the molecule. Various methods have been proposed for creating randomized libraries of nucleic acids that code for proteins containing all or selected amino acids. (e.g. U.S. Pat. No. 5,869,644, WO 0000632, WO 0018778) For instance, if the mRNA does not contain any codons that code for lysine, the protein (capture agent) will not contain any lysine after translation. However, a strictly combinatorial preparation of a library of mRNA that does not contain lysine codons (AAA and AAG) would give rise to the library also lacking many other important amino acids that are likely to be important in the binding event. Leaving the codons intact, but limiting the ability of the system to incorporate lysine by either omitting lysine from the in vitro reaction or depleting the lysine charged tRNA by prior reaction with poly (AAA) or poly (AAG) would effectively give rise to stop codons wherever a lysine would have been. Because of the two additional stop codons, this would give a library consisting of a number of shorter polypeptides along with the desired products.

EXAMPLE 3 mRNA library formation could be done in a fashion so that no "A" is present in the third position of the codon. This will not eliminate any amino acids from the combinatorial library. In addition, the prior depletion of the tRNA (AAG codon) would eliminate the lysines, and result in only one additional "stop" codon. This library will have fewer short peptides than the method described in example 2. This technique or similar techniques can be applied for a variety of amino acids which one desires to exclude from the polypeptide chain.

EXAMPLE 4

Other ways to ensure that the capture agent does not include lysine or a particular amino acid, but maintain the possibility of having all the other amino acids present are possible. After the translation of the mRNA library into a mixture of fusion proteins (potential capture agents), the proteins that contain lysine or similar residues can be selectively removed by chemical reaction with an amine reactive solid support, or by selective reaction of the lysine or amino acid residue with a biotinylated reagent for subsequent separation on an avidin coated surface. In order to remove the reactive primary N-terminal amine, the amino termini of all the molecules will need to first be deactivated. This can be accomplished, for example, by chemical or enzymatic reaction, by the use of prokaryotic translation systems that would give a blocked formylated N-terminus, or by creating libraries of 5'nucleic acid conjugates (WO 0072869). Once the amine containing proteins are removed from the library, the selection process can be performed in a standard fashion, giving rise to a capture agent that does not contain lysine.

EXAMPLE 5

Another way of ensuring that the capture agent does not contain any of the undesired amino acids, e.g. lysine, is to isolate a number of potential capture agents and afterwards select only those that do not contain lysine. The presence or absence of lysine in the capture agent can be ascertained by standard biological techniques, e.g. by sequencing the cDNA associated with protein, by sequencing the protein directly, or by performing an amino acid analysis on the protein.

EXAMPLE 6

It is not necessary to actually omit in the capture agents the amino acids that are reactive to the labeling agent. It is sufficient that the side chains of these amino acids are blocked, either during or after the selection process. For some capture agents, blocking the pertinent side chains after the selection process will result in a capture agent that still retains the ability to bind to the target. For example, reacting the capture agent with the N-hydroxylsuccinimide ester of acetic acid (NHS acetate) will alter the amino groups of the lysine side chains. If these side chains are not involved in the target binding event, a viable capture agent is produced that will not react with an amine reactive labeling agent Derivatizing the side chains of potential capture agents before the selection process is made will result in a capture agent that is optimized for binding while at the same time will not contain a reactive side chain. For example, a library of ribosome or phage displayed proteins is treated with an amine reactive reagent such as NHS acetate. After reaction, the amines on the lysines and the N-terminal are blocked as the acetamide. The selection process is performed with this derivitized mixture. Capture agents that are isolated by this process will have an affinity for the target, but will contain lysine in which the side chains are present as an acetamide, and will not be reactive to amine reactive labeling reagents. It is possible that during the amine blocking process the tertiary structure of the capture agent may be such that the amines are resistant to derivatization and will not react with NHS acetate. If this is the case, it is likely that the amines will be likewise resistant to reaction with an amine reactive labeling agent.

Instead of derivatizing the lysines to form an acetamide, it is also possible to form derivatives that can have strong interactions with the targets, thereby possibly increasing the affinity of the capture agents for the target. An example of this is the reaction of lysine with the NHS ester of a carboxylic acid containing a quaternary ammonium group; transforming a reactive positively charged side chain (primary amine) into an unreactive positively charged side chain (quarternary amine). Another example is the reaction of a cysteine with iodoacetic acid, transforming a neutral side chain into one containing a negative charge.

EXAMPLE 7

Another way to ensure that the capture agent does not contain lysine or another amino acid is to use known methods for incorporating alternative amino acids for a given mRNA codon. (e.g. Gilmore, M. A., Steward, L. E., Chambelin, A. R., "Incorporation of non-coded amino acids by in vitro protein biosynthesis", Top Curr. Chem 202: 77–99 (1999), Brunner, J. "Biosynthetic incorporation of non-natural amino-acids into proteins", Chem. Soc. Rev. 22: 183–189 (1993)). These methods usually involve using a tRNA with an anti-codon that matches what is normally a stop codon. A wide variety of unnatural amino acids can be incorporated during translation of the protein by pre-acylating this tRNA molecule. Such a system could be readily modified to insert a lysine "replacement" at the appropriate mRNA condons, which in the case of lysine are AAA and AAG. Natural analogues such as arginine, or even unnatural amino acids such as trimethyllysine, or other types of amino acids or analogues could be inserted in place of lysine. In order to keep the "normal" tRNA from inserting lysine, the in vitro translation could be done in the absence of lysine or lysine charged tRNA could be depleted by adding poly (AAA) or poly (AAG) to the reaction mixture. An analogous scheme could be used to replace any desired amino acid with a different amino acid.

EXAMPLE 8

The capture agents produced by the procedures described would not have lysine present, or the lysine amino groups would be unreactive. Such a system could be attached to a protein array chip through the N-terminus or through the mRNA of a fusion protein (e.g.WO 9951773). In the case where amino functionalities, including the N-terminus are unavailable for reaction with the surface, for example in those cases where the selection of the capture agent is done using a library containing acetamide derivitized primary amines, as described in Example 6, a subsequent amplification and translation step could involve the addition of a single or multiples lysines at one end of the protein. This would also allow for covalent attachment to the array surface through a primary amine. After surface attachment, residual amines, if present, could be blocked as previously described. Specific attachment through other amino acids that could be incorporated deliberately during the translation process is also possible (e.g. a chain of aspartic acids or histidines). In cases where the N-terminus is still present (e.g., those methods involving tRNA manipulation as described in Example 7), the primary alpha amino group can be used for the surface attachment. There are numerous other methods known for attachment of peptides to surfaces. For the purposes of this invention, attachment methods are only limited insofar as there can be no groups present after attachment that will react with the desired labeling agent.

EXAMPLE 9

An array is prepared that contains the desired capture agents bound to the surface. The array is exposed to a sample containing the target mixture, under conditions that will allow specific binding of a given target to its respective capture agent. After washing to remove non-specifically bound target molecules, the array is treated with a suitable labeling agent. For example, in the case of a capture agent that has no reactive amines present, a bound target that contains reactive amines is tagged using the NHS ester of Cy3, or the Attotag© labeling system (Molecular Probes). Array sites that do not contain any bound amine-containing target will remain unlabeled. After washing if neccessary to remove unreacted labeling reagent (in the case of Cy3), the target binding on the array is ready to be quantitated using a fluorescent scanner.

When a user receives an array made by an apparatus or method of the present invention, it will typically be exposed to a sample during which time targets present in the sample will bind to the capture agents at specific locations on the array. After subsequent labeling of the bound target, the array is interrogated. Interrogation is usually accomplished by a suitable scanner that can read the location and intensity of fluorescence at each feature of an array. For example, such a scanner may be similar to the GENEARRAY scanner available from Agilent, Inc., Palo Alto, Calif. Results from the interrogation can be processed results, such as obtained by rejecting a reading for a feature which is below a predetermined threshold and/or forming conclusions based on the pattern read from the array (such as whether or not a particular target sequence may have been present in the sample). The results of the interrogation (processed or not) can be forwarded (such as by communication) to a remote location if desired and received there for further use.

Various modifications to the embodiments of the invention described above are, of course, possible. Accordingly, the present invention is not limited to the particular embodiments described in detail above.

REFERENCES

Roberts, R. W., Szostak, J. W. "RNA-peptide fusions for the in vitro selection of peptides and proteins" P. Natl Acad. Sci. USA 94: 12297–12302 (1997).

Wilson, D. S. Szostak, J. W. "In vitro selection of functional nucleic acids", Annu Rev. Biochem. 68: 611–647 (1999).

Gilmore, M. A., Steward, L. E., Chambelin, A. R., "Incorporation of non-coded amino acids by in vitro protein biosynthesis", Top Curr. Chem 202: 77–99 (1999).

Brunner, J. "Biosynthetic incorporation of non-natural amino-acids into proteins", Chem. Soc. Rev. 22: 183–189 (1993).

Creighton, T. E., Proteins, Structure and Molecular Properties, Second Edition, W. H. Freeman & Company, New York, 1993; pp. 86–104.

Creighton, T. E., Protein Function, A Practical Approach, Oxford University Press, New York, 1990; pp. 101–132; 225–274.

Janeway, C. A., Travers, P., Walport, M. & Capra, J. D., ImmunoBiology, The Immune System in Health and Disease, Fourth Edition, Elsevier Science Ltd., Garland Publishing, New York;1999; pp.101–132; 225–274.

WO 9831700

WO 004775

WO 0032823

U.S. Pat. No. 5,86,9644

WO 0000632

WO 0018778

WO 0072869

I claim:

1. A method for determining whether a target molecule is present in a sample, comprising:
   (a) contacting a sample with an array of polypeptide capture agents comprising a polypeptide capture agent that specifically binds to a target molecule;
   (b) contacting the array produced by step (a) with a labeling agent that covalently bonds to the target molecule but not to the polypeptide capture agents; and
   (c) detecting any resultant covalently bound labeling agents to determine whether the target molecule is present or absent in the sample.

2. The method according to claim 1, wherein the labeling agent covalently bonds to an amino acid of the target molecule that is not present in the polypeptide capture agents.

3. The method according to claim 1, wherein said the labeling agent covalently bonds to an amino acid of the target molecule that is present but non-reactive in the polypeptide capture agents.

4. The method according to claim 3, wherein the amino acid in the polypeptide capture agent is blocked.

5. The method according to claim 1, wherein an amino acid of the target molecule contains a side chain that covalently bonds to the labeling agent.

6. The method according to claim 1, wherein an amino acid of the target molecule is selected from the group consisting of lysine, arginine, cysteine, glutamic acid and aspartic acid.

7. The method according to claim 1, wherein the labeling agent comprises a fluorophore.

8. The method according to claim 1, wherein the labeling agent comprises a radioisotope.

9. The method according to claim 1, wherein the target molecule is a protein molecule.

10. The method according to claim 1, wherein the target molecule of step (a) is non-modified.

11. The method according to claim 1, wherein the method, after completion of step (a), further comprises contacting the array with a washing agent to remove any unbound and non-specifically bound target molecules.

12. The method according to claim 1, wherein the method is quantitative.

13. A method for determining whether a target molecule is present in a sample, comprising:
   (a) contacting a sample with an array of polypeptide capture agents comprising a polypeptide capture agent that specifically binds to a target molecule;
   (b) contacting the array produced by step (a) with a labeling agent that covalently bonds to the target molecule by covalently bonding to an amino acid of the target molecule that is not present in the polypeptide capture agents; and
   (c) detecting any resultant covalently bound labeling agents to determine whether the target molecule is present or absent in the sample.

14. The method according to claim 13, wherein the amino acid of the target molecule contains a side chain that covalently bonds to the labeling agent.

15. The method according to claim 13, wherein the amino acid of the target molecule is selected from the group consisting of lysine, arginine, cysteine, glutamic acid and aspartic acid.

16. The method according to claim 13, wherein the labeling agent comprises a fluorophore.

17. The method according to claim 13, wherein the target molecule is a protein molecule.

18. The method according to claim 13, wherein the target molecule of step (a) is non-modified.

19. The method according to claim 13, wherein the method, after completion of step (a), further comprises contacting the array with a washing agent to remove any unbound and non-specifically bound target molecules.

20. The method according to claim 13, wherein the method is quantitative.

21. A method for determining whether a target molecule is present in a sample, comprising:
   (a) contacting the sample with an array of polypeptide capture agents comprising a polypeptide capture agent that specifically binds to the target molecule;
   (b) contacting the array produced by step (a) with a labeling agent that covalently bonds to said the target molecule by covalently bonding to an amino acid of the target molecule that is present but non-reactive in the polypeptide capture agents; and
   (c) detecting any resultant covalently bound labeling agents to determine whether the target molecule is present or absent in the sample.

22. The method according to claim 21, wherein the amino acid in the polypeptide capture agent is blocked.

23. The method according to claim 21, wherein the amino acid of the target molecule contains a side chain that covalently bonds to the labeling agent.

24. The method according to claim 21, wherein the amino acid of the target molecule is selected from the group consisting of lysine, arginine, cysteine, glutamic acid and aspartic acid.

25. The method according to claim 21, wherein the labeling agent comprises a fluorophore.

26. The method according to claim 21, wherein the target molecule is a protein molecule.

27. The method according to claim 21, wherein the target molecule of step (a) is non-modified.

28. The method according to claim 21, wherein said the method, after completion of step (a), further comprises contacting the array with a washing agent to remove any unbound and non-specifically bound target molecules.

29. The method according to claim 21, wherein the method is quantitative.

* * * * *